United States Patent [19]

Swartz et al.

[11] Patent Number: 5,470,347
[45] Date of Patent: Nov. 28, 1995

[54] SAFETY MONITOR CIRCUIT FOR AN ECT DEVICE AND METHOD

[75] Inventors: Conrad M. Swartz, Greenville, N.C.; Richard S. Abrams, Vernon Hills, Ill.

[73] Assignee: Somatics, Inc., Lake Bluff, Ill.

[21] Appl. No.: 354,612

[22] Filed: Dec. 13, 1994

[51] Int. Cl.⁶ ............................................. A61N 1/18
[52] U.S. Cl. ................................................. 607/45; 607/63
[58] Field of Search .................................... 607/63, 45, 46

[56] References Cited

U.S. PATENT DOCUMENTS 4,177,819  12/1979  Kofsky et al. ........................ 607/63
4,503,863  3/1985  Katims .................................. 607/64

Primary Examiner—William E. Kamm
Assistant Examiner—Scott M. Getzow
Attorney, Agent, or Firm—Eliot S. Gerber

[57] ABSTRACT

An electronic method and apparatus in electroconvulsive therapy (ECT) to automatically measure the electrical dosage of an ECT device at the time of stimulus and to prevent delivery to the patient of a dosage that is substantially (e.g., more than 5%, or 25 millicoulombs [mC], or 5 joules [J]) larger than the dosage selected by the operator. When the measured dosage varies more or less than a selected limited amount, or proportion, from the stimulus dial setting (e.g., 5% or 25 mC or 5 J), visible and/or audible signals are triggered and the device is blocked from delivering further stimuli without first being reset.

17 Claims, 4 Drawing Sheets

SAFETY MONITOR CIRCUIT FOR AN ECT DEVICE AND METHOD

BACKGROUND OF THE INVENTION

1. Field of the Invention

The present invention relates to medical apparatus and methods and more particularly to electroconvulsive therapy (ECT) apparatus and method for preventing an excessive or insufficient stimulus dosage.

2. Description of the Related Art

In electroconvulsive therapy (ECT), using "bitemporal" electrode positioning, generally two electrodes are applied to the temple of the patient during the treatment session. One electrode is positioned on the temple's left side and the other on the temple's right side. A small electric current, called the "stimulus dosage", is applied for less than ten seconds between the two electrodes. Alternatively, the electrodes may be positioned anterior bilaterally or unilateral. Only a small portion of the current reaches the brain because most is deflected by the skull.

It has recently been shown that when administered according to accepted standard of practice (American Psychiatric Association, APA, 1990). electroconvulsive therapy (ECT) is a safe procedure that does not have a measurable risk of brain injury. The APA standard of practice includes a limitation of the stimulus dosage administered to the patient, because of the expectation that unnecessarily high stimulus dosages may cause adverse effects to the patient. To accomplish the delivery of a stimulus dosage within operator specifications, i.e., the stimulus dosage determined by the attending physician, existing ECT devices rely on a calibration, or test, conducted prior to initiation of the stimulus or during periodic maintenance checks on the ECT device. Once the stimulus dosage has been initiated, delivery of an accurate dose, for example, within the APA standard, has relied solely on the circuits of the ECT device that generate the stimulus. There has been no separate circuit or device to monitor and measure the stimulus dosage during its application, and to terminate the stimulus in the event it exceeds the operator's specification, i.e., the operator's setting of the dosage on a dial of the ECT device.

In the event of failure of an electronic component it is possible for existing ECT devices to deliver an electrical stimulus dose that substantially exceeds the operator's specification. It is also possible that such a dosage would exceed the maximum indicated by a national or international agency that publishes, or could publish, standards for ECT devices, e.g., the IEC—International Electrotechnical Commission 601-2-14; the APA—American Psychiatric Association; the FDA—Food and Drug Administration. Such an excessive dosage may inadvertently, and unnecessarily, expose the patient to a dose that exceeds the published limitations for ECT devices.

A "worst-case" scenario would be the exposure of the patient to line current, as might occur in failure of the ECT device's transformer, for example, a transformer short circuit due to insulation breakdown. Although the likelihood of such an occurrence is extremely remote, such a possibility must nevertheless be considered because of the life and death nature of such exposure.

Existing test methods employed to evaluate the safety of the stimulus prior to ECT are limited to measuring the skin impedance of the patient by applying impalpable electrical trickle currents to the patient's skin. However, such skin impedance test circuits cannot prevent the patient from receiving an excessive electrical dosage that may be delivered in the event of component failure in the ECT device, because such skin impedance test circuits do not monitor the actual stimulus.

In ECT, the physician determines the stimulus dosage, i.e., the length and strength of the applied current. He takes into account such factors as the patient's age, size, physical condition and prior history of ECT treatments. The seizure threshold systematically increases with age. The physician may, with presently available apparatus, reasonably and accurately select the desired electrical duration. For example, in the "Thymatron-DGx" ECT instrument (TM of Somatics, Inc., Lake Bluff, Ill.) the stimulus may be selected to be a brief series of electrical square waves, providing a constant current of 0.9 amps limited to 500 volts, consisting of 60–140 bipolar pulses per second of 1 msec width, which is adjustable, by the physician, 0.1–8.0 second in duration. Alternatively the dosage may be administered in groups of pulses, pacing them over a period of up to 8 seconds.

Generally the physician will determine the stimulus dosage and set that selection in the ECT device by setting a stimulus dial. The ECT device, in the case of the "Thymatron-DGx" device, has factory preset pulsewidth, frequency and duration which corresponds to each stimulus dial setting. Alternatively, the physician may elect to set other pulsewidths, frequencies and durations within the range 30–70 Hz and 0.5 to 1.5 msec.

In U.S. Pat. No. 5,269,302 to Swartz and Abrams, an ECT device includes a special-purpose electromyograph (EMG) to detect muscle activity. In U.S. Pat. No. 4,873,981 to Abrams and Swartz the ECT device includes a system to automatically monitor and display the occurrence and duration of an induced EEG seizure. In U.S. Pat. No. 4,709,700 to Hyrman an ECT device uses short pulses of 20–100 microseconds and unidirectional electric direction. The Hyrman patent, incorporated by reference herein, discusses the techniques of "ergometry" (measurement of ECT dose in pulses) and "coulometry" (total charge which flows during treatment).

SUMMARY OF THE INVENTION

The present invention presents a method and system to automatically monitor and measure the cumulative stimulus dosage of an ECT device. The dosage produced at the output terminals of an ECT device, during stimulus delivery, is measured by a separate excessive output control circuit which is preferably integrated into the ECT instrument. A known portion of the stimulus from an output driver is first passed through a pulse transformer or opto-isolator. The cumulated dosage of that stimulus is measured by a completely separate analog or digital excessive output control circuit. Since the excessive output control circuit is completely separate from the main circuitry of the ECT device, except for its power supply, any fault in the main circuitry, such as its microprocessor CPU, will not affect the separate excessive output control circuit, since it has its own microprocessor CPU, etc. The stimulus is automatically compared to the stimulus dose set by the operator using a percent energy selector, which is preferably a dial on the ECT device.

In the event of an "excessive dosage" further stimulus delivery is automatically blocked and audible and/or visual signals are activated. An "excessive dosage" is when a predetermined increment (e.g., 5%, or 25 millicoulombs [mC] or 5 Joules [J]) over the specified dosage has been delivered. If the stimulus dosage which is actually delivered is less than a predetermined threshold (below the operator's specification for the stimulus dosage), a different set of audible and/or visual signals are triggered.

OBJECTIVES AND FEATURES OF THE INVENTION

It is an objective of the ECT instrument to provide a stimulus dosage that conforms with reasonable accuracy (e.g., within 5%, 25 mC, 5 J) to the specification set by the operator using the ECT instrument's controls.

It is a further objective of the present invention that the physician may directly set the electrical charge of the stimulus dosage, in millicoulombs (mC), and that dosage will be delivered within a selected limit, for example, 5% of the selected dosage.

BRIEF DESCRIPTION OF THE DRAWINGS

Other objectives of the present invention will be apparent from the following detailed description, which should be taken in conjunction with the accompanying drawings. In the drawings.

DETAILED DESCRIPTION

In accordance with the present invention there is provided a system and method in ECT to automatically measure and monitor the cumulative amount of electrical dosage given to a patient in each ECT treatment session. If the amount of dosage is in excess of the amount selected by a predetermined limit, the application of the dosage is immediately and automatically halted. In addition, the attending physician is warned of the excessive dosage by a warning light and/or an audio signal. On the other hand, if the dosage is below the selected dosage by a predetermined limit, the physician is warned by a different light and/or audio signal. Preferably, in that case, the percentage of dosage that has been applied is displayed; for example, a display may say "20%", indicating 20% below the selected dosage.

Preferably the ECT system of the present invention is incorporated as part of an ECT device; however, it may be possible to retrofit it into some existing ECT devices, depending on their circuitry.

The limits may be set in a number of ways. For example, a limit may be set as being plus and minus 5% of the selected dosage. If the dosage is 100 J (Joule) then the 5% limit would be 5 J and an excessive dosage would be 105 J and an insufficient dosage would be 95 J or less. Alternatively, the plus and minus limits may be set as an arbitrary amount of charge dosage, for example, plus and minus 25 mC (25 milliCoulombs) over a range of from 25 mC to 500 mC.

In general, the amount of electrical power that is generated by the ECT device and applied to the patient is measured by sampling the power furnished at the output electrode of the device. Such sampling is preferably performed in a circuit parallel to the output circuit.

The present invention provides circuitry to monitor the stimulus dosage of electrical current as it is actually applied to the patient. It operates in "real time" (immediately) thereby automatically limiting the dosage, to within a predetermined amount, of the dosage specified by the operator, e.g., the attending physician.

Figure 1:
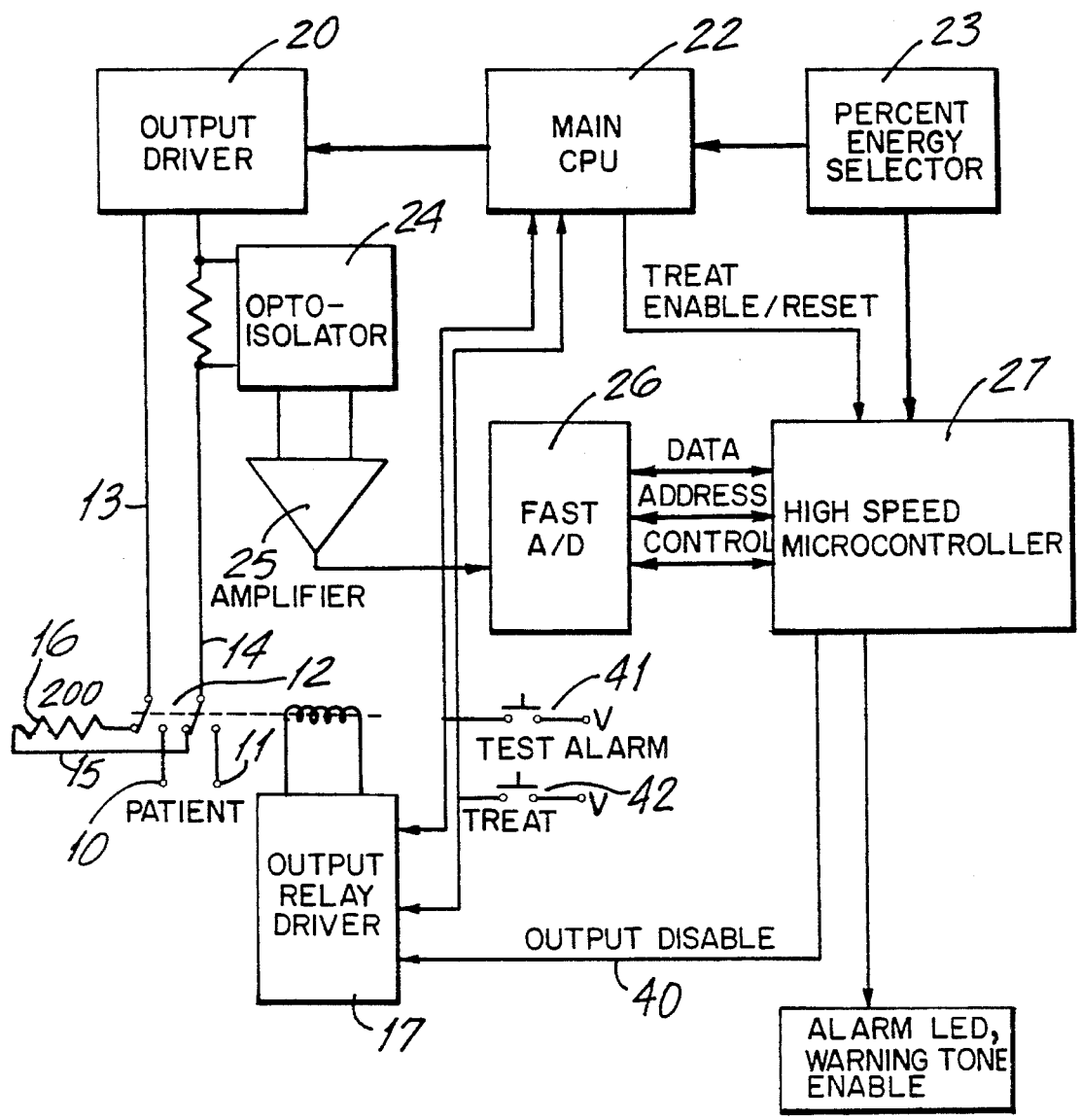
FIGS. 1 and 2 are block circuit diagrams of a preferred embodiments of the present invention.
Figure 2:
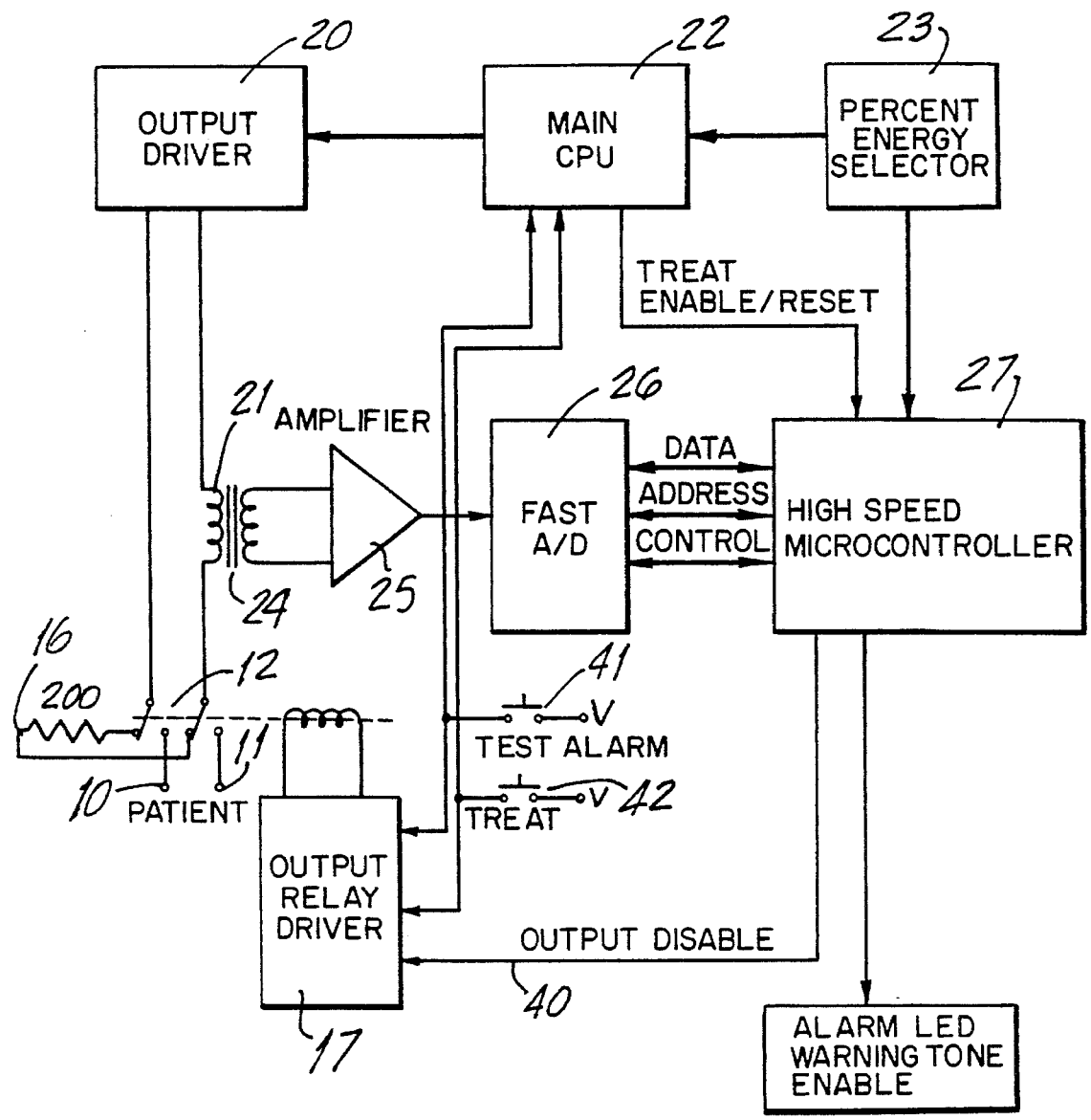

The circuitry for two alternative "high end" alarm and control circuits is shown in FIGS. 1 and 2. The bitemporal electrodes 10 and 11 are adapted to be removably attached to the temple of the patient at the left and right sides. A single-double-pole double-throw (DPDT) relay switch 12 connects the lines leading to the electrodes 10 and 11 either to the output lines 13 and 14 or to the dummy load line 15 having a 200 ohm resistor 16. The switch 12 is operated by the output relay driver 17.

The output driver 20, which is generally the secondary winding of a transformer, provides the current for the stimulus dosage generally as a sine wave or rectangular waves. The output driver 20 is controlled by the main "CPU" (Central Processing Unit) 22 which preferably is a solid-state integrated circuit ("IC") and is preferably a microprocessor such as a Motorola 68306 (TM of Motorola, Inc., Schaumburg, Ill.). The main CPU 22 is connected to the Percent Energy Selector 23 which preferably is a dial of the ECT device. The dial is set by the operator to select the desired stimulus dosage.

In the embodiment of FIG. 1 an opto-isolator 24 is connected in parallel to line 14, a suitable opto-isolator being Siemens IL300. The output of the opto-isolator 24 is to amplifier 25.

In the embodiment of FIG. 2 a primary winding 21 of pulse transformer 24 provides a sample of the current on line 14 which is amplified by amplifier 25.

In the embodiments of FIGS. 1 and 2 the output of amplifier 25 is to Fast A/D (Analog-Digital converter) 26. The Fast A/D 26 is connected for data transfer ("Data"), address information ("Address") and control ("Control") to High Speed Microcontroller 27, for example, a Motorola 68306. The microprocessor 27 enables (controls the Alarm LED (Light Emitting Diode) and warning tone 28 (audio generator).

In the embodiments of FIGS. 1 and 2 the electrical output at the output driver 20 is in the form of a regular waveshape, generally a sine wave or rectangular wave. That output waveform is sampled at a high rate, for example, 100,000 times a second, and the analog samples are converted to digital data by the Fast A/D converter 26. The digital data (Data) is transferred from Fast A/D 26 to a high-speed programmable microcontroller 27 having an internal RAM (Random Access Memory). The RAM is programmed with a look-up table in which the selected dosage, selected by Percent Energy Selector 23, has been entered and a corresponding different selected limit for each selected dosage has also been entered. Preferably the selected limit is automatically calculated for each selected dosage by a programmed algorithm entered into the microprocessor and then the selected limit is entered into the RAM look-up table.

If the limit is exceeded the microcontroller 27 will generate an inhibit control signal, which is the "output disable" signal on line 40 to relay driver 17, to terminate the dosage. Such termination can be accomplished in less than 1/100th of a second so that the excess dosage would be less than 1% over the selected limit. In addition, that control signal, or a subsequent signal generated by the microcontroller 27, will activate the warning device 28 to call the attending physician's attention to the excessive dosage. Preferably a warning lamp is lit and/or an audio signal, such as a buzz, is produced.

If the selected dosage is not reached, the ECT device will automatically notify the physician that the dosage was insufficient and will display the amount of the insufficiency. Preferably a different warning light and/or audio sound is used and the amount of insufficiency is displayed on a numerical display panel of the ECT device and/or printed by a connected alphanumeric printer.

Figure 3:
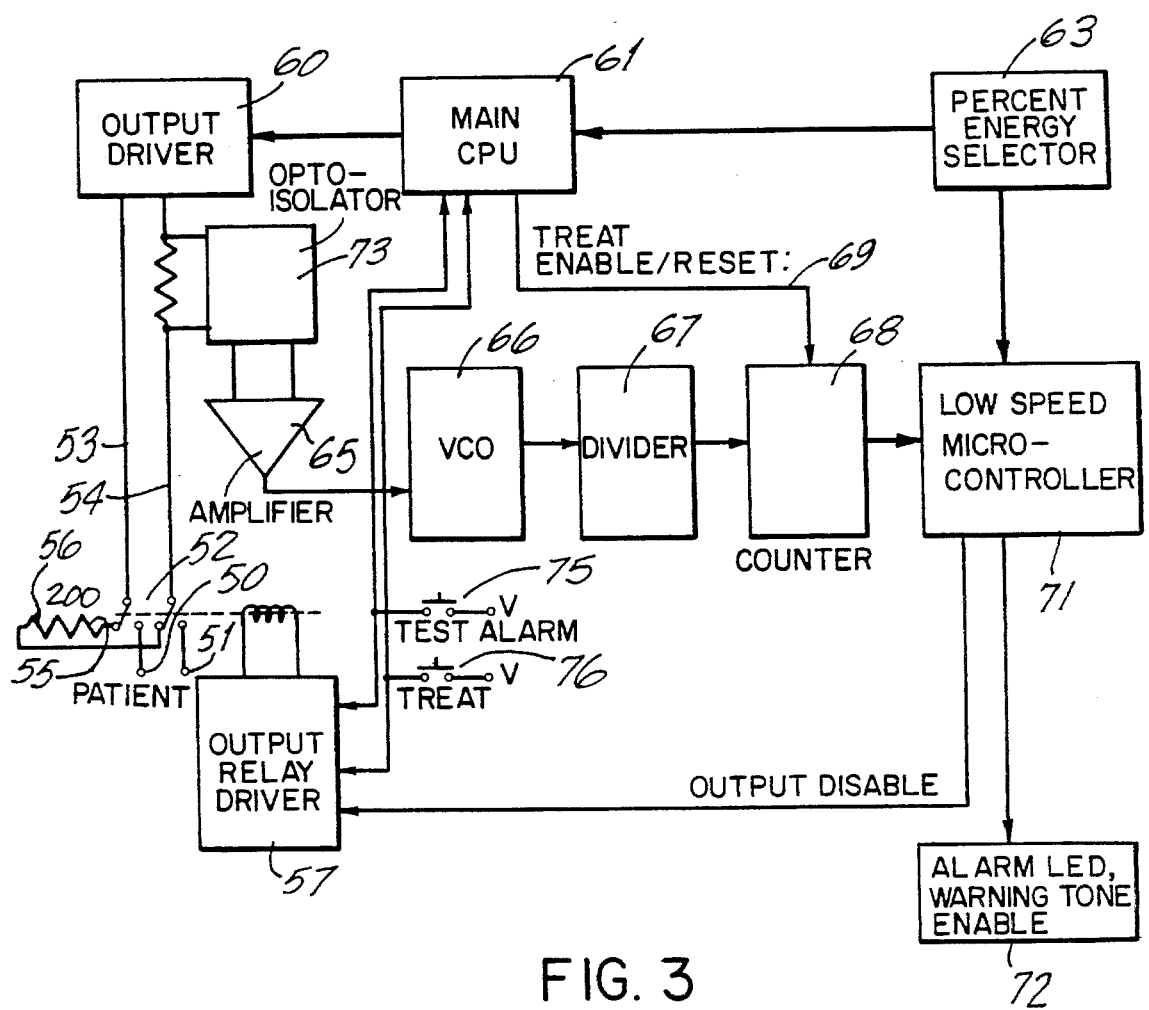
FIGS. 3 and 4 are block circuit diagrams of an alternative lower-cost circuits of the present invention.
Figure 4:
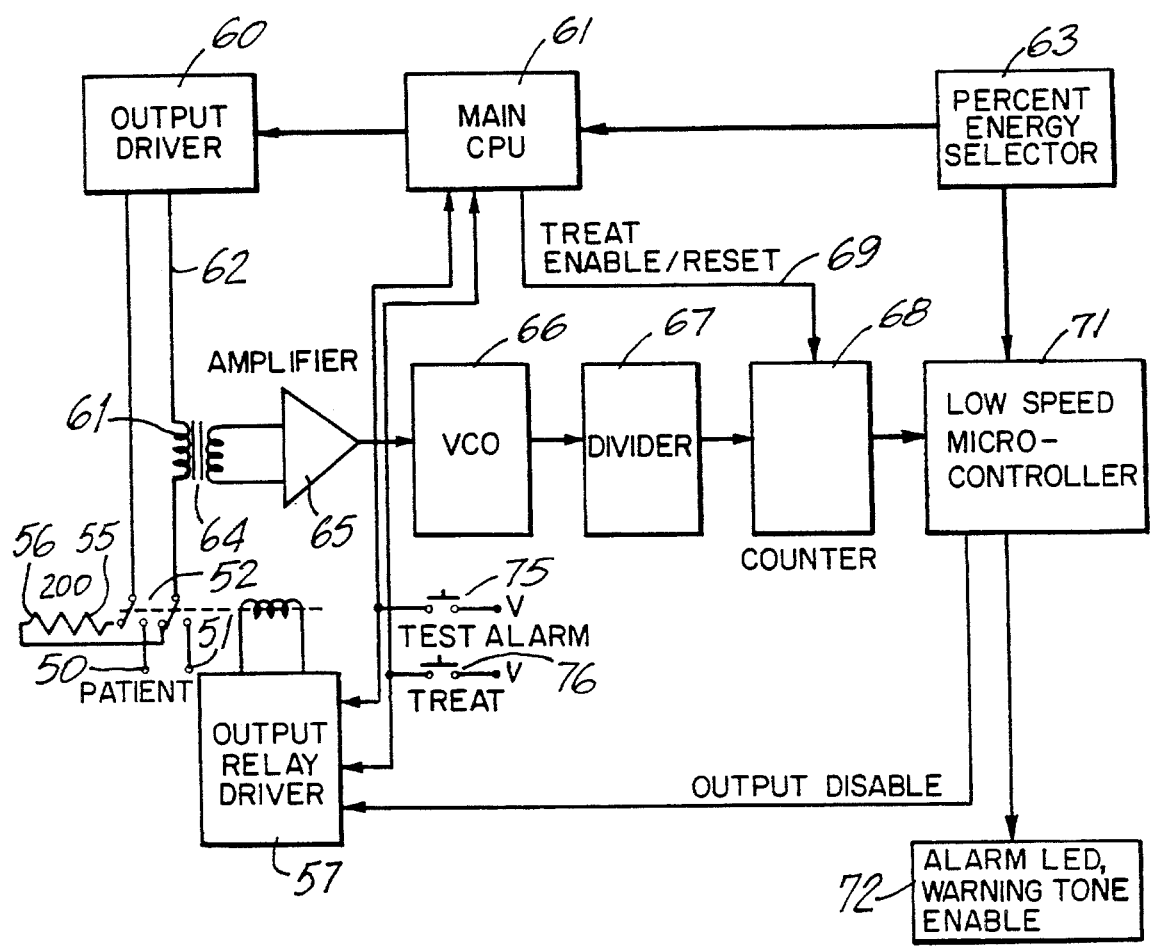

Two "low end" alternatives (shown in FIGS. 3 and 4) to the "high end" use of a high-speed A/D converter and high-speed microprocessor, as in FIGS. 1 and 2, use an oscillator which is connected in parallel to the output electrodes of the ECT device. In the circuit of FIGS. 3 and 4, an oscillator (VCO—Voltage Controlled Oscillator) is configured to act as a voltage-to-frequency converter in which a rising voltage is measured and converted to a higher frequency rate. The pulses from the VCO (Voltage Controlled Oscillator) are connected through a divider 67 to a counter 68. The output of counter 68 is processed by a low-speed microprocessor. The use of a RAM look-up table, the control signals and the warnings are preferably the same as in the prior embodiment.

The circuitry for a "low end" alarm and control circuits are shown in FIGS. 3 and 4. The bitemporal electrodes 50 and 51 are adapted to be removably attached to the temple of the patient at the left and right sides. A double-pole double-throw (DPDT) relay 52 connects the lines leading to the electrodes 51 and 52 either to the output lines 50 and 51 or to the dummy load line 55 having a 200 ohm resistor 56. The switch 52 is operated by the output relay driver 57.

The output driver 60, which is generally the secondary winding of a transformer, provides the current for the stimulus dosage. The output driver 60 is controlled by the main "CPU" (Central Processing Unit) 61 which preferably is a solid-state integrated circuit ("IC") and is preferably a microprocessor such as Motorola 68306. The main CPU 61 is connected to the Present Energy Selector 63 which preferably is a dial on the ECT device. The dial is set by the operator to select the desired stimulus dosage.

In the embodiment of FIG. 3 an opto-isolator 73 is connected in parallel to line 54, a suitable opto-isolator being Siemens IL 300. The output of opto-isolator 73 is to amplifier 55.

In the embodiment of FIG. 4 the primary winding 61 of pulse transformer 64 provides a sample of the current on line 61 which is amplified by amplifier 65.

In the embodiments of FIGS. 3 and 4 the output from amplifier 65 is to VCO (Voltage Controlled Oscillator) 66 whose output is to divider 67. The divider 67 is connected to counter 68 which is controlled over line 69 from CPU 62. The counter 68 is connected to a low-speed microcontroller 71, for example, Intel 8051 (TM, Intel) which also is connected to Percent Energy Selector 63. The output 71 is to the Alarm 72, which preferably is an LED (Light Emitting Diode) and a warning tone generator.

The circuits are provided with a manually operated test alarm switch (41 in FIGS. 1 and 2; 75 in FIGS. 3 and 4) and a manually operated on-off start of treatment switch (42 in FIGS. 1 and 2; 76 in FIGS. 3 and 4).

What is claimed is:

1. An electroconvulsive therapy (ECT) system to apply an ECT dosage selected by an operator to a patient, the system comprising:

(a) electrodes adapted to be removably connected to the head of the patient;

(b) ECT dosage selection means to permit the operator to select the ECT dosage for the patient;

(c) an output driver means connected to the electrodes and to the ECT dosage selection means to generate the ECT dosage;

(d) a sampling circuit means to sample the ECT dosage;

(e) a switch means having open and closed positions connected between the output driver means and the electrodes;

(f) a limit circuit means connected to the sampling circuit means and the switch means to generate a control signal to operate the switch means to the open position upon sensing an excess ECT dosage in excess of a predetermined amount greater than the ECT dosage selected for the patient.

2. An electroconvulsive therapy (ECT) system as in claim 1 comprising two electrodes adapted to be removably connected at a patient's temple and connected to the output driver.

3. An electroconvulsive therapy (ECT) system as in claim 1 wherein the output driver means generates a train of rectangular waves.

4. An electroconvulsive therapy (ECT) system as in claim 1 wherein the output driver means generates a train of square waves.

5. An electroconvulsive therapy (ECT) system as in claim 1 wherein the output driver means includes an opto-isolator.

6. An electroconvulsive therapy (ECT) system as in claim 1 wherein the output driver means includes a pulse transformer.

7. An electroconvulsive therapy (ECT) system as in claim 1 wherein the sampling circuit means includes a transformer having a primary coil and a secondary coil and wherein the primary coil is connected between the output driver and the electrodes.

8. An electroconvulsive therapy (ECT) system as in claim 7 wherein the sampling circuit means includes an amplifier connected to the secondary coil.

9. An electroconvulsive therapy (ECT) system as in claim 1 wherein the sampling circuit includes an Analog/Digital converter and a microcontroller having a memory with a look-up table, the look-up table having a set of ECT dosage selections and a predetermined limit amount corresponding to each ECT dosage selection.

10. An electroconvulsive therapy (ECT) system as in claim 1 wherein the ECT dosage selection means includes a number setting device.

11. An electroconvulsive therapy (ECT) system as in claim 1 and further including a warning means which is connected to and controlled by the limit circuit means to provide a warning of the excess ECT dosage.

12. An electroconvulsive therapy (ECT) system as in claim 11 wherein the warning means provides a warning if ECT dosage is below the selected ECT dosage selection by a predetermined amount.

13. An electroconvulsive therapy (ECT) method to apply to a patient an ECT dosage generated by an ECT device and selected as to amount of dosage by an operator, the method comprising:

(a) removably connecting electrodes to the head of the patient;

(b) selecting the ECT dosage for the patient by operation of an ECT dosage selector on the ECT device;

(c) using an output driver means of the ECT device which is connected to the electrodes and to the ECT dosage selector to generate the ECT dosage;

(d) using a sampling circuit means of the ECT device to sample the ECT dosage; the ECT device having a switch means with open and closed positions connected between the output driver means and the electrodes; and (e) generating a control signal from a limit circuit means of the ECT device which is connected to the sampling circuit means and the switch means to operate the switch means to the open position upon sensing an excess ECT dosage in excess of a predetermined limit amount greater than the ECT dosage selected for the patient.

14. An electroconvulsive method (ECT) as in claim 13 and further including removably connecting two electrodes at a patient's temple, the electrodes being connected to the output driver.

15. An electroconvulsive therapy (ECT) method as in claim 13 and further including electrically isolating the electrodes using an opto-isolator in the output driver.

16. An electroconvulsive therapy (ECT) method as in claim 13 and further warning of the excess ECT dosage using a warning means which is connected to, and controlled by, the limit circuit means.

17. An electroconvulsive therapy (ECT) device as in claim 13 wherein a warning means provides a warning if ECT dosage is below the selected ECT dosage selection by a predetermined amount.

* * * * *